United States Patent
Gottschlich et al.

[19]

[11] Patent Number: 6,118,021
[45] Date of Patent: Sep. 12, 2000

[54] MEMBRANE PROCESS FOR ARGON PURGING FROM VINYL ACETATE REACTORS

[75] Inventors: Douglas Gottschlich, Mountain View; Richard W. Baker, Palo Alto, both of Calif.

[73] Assignee: Membrane Technology and Research, Inc., Menlo Park, Calif.

[21] Appl. No.: 09/166,296

[22] Filed: Oct. 5, 1998

Related U.S. Application Data

[63] Continuation-in-part of application No. 08/890,856, Jul. 10, 1997, Pat. No. 5,817,841.

[51] Int. Cl.[7] .................................................. C07C 67/05
[52] U.S. Cl. ...................... 560/243; 560/241; 560/241.1; 560/245
[58] Field of Search .............................. 560/241, 241.1, 560/243, 245

[56] References Cited

U.S. PATENT DOCUMENTS

| | | | |
|---|---|---|---|
| 3,444,189 | 5/1969 | Olivier | 260/497 |
| 3,547,983 | 12/1970 | Mottern et al. | 260/488 |
| 3,557,191 | 1/1971 | Copelin | 260/497 |
| 3,716,581 | 2/1973 | Calcagno et al. | 560/243 |
| 3,855,280 | 12/1974 | Severs, Jr. | 560/245 |
| 3,970,713 | 7/1976 | Scharfe et al. | 568/877 |
| 3,989,742 | 11/1976 | Calcagno et al. | 560/243 |
| 4,370,150 | 1/1983 | Fenstermaker | 95/49 |
| 4,553,983 | 11/1985 | Baker | 55/16 |
| 4,857,078 | 8/1989 | Watler | 55/16 |
| 4,879,396 | 11/1989 | Ozero | 549/534 |
| 4,880,441 | 11/1989 | Kesting et al. | 95/47 |
| 4,904,807 | 2/1990 | Ozero | 549/534 |
| 4,906,256 | 3/1990 | Baker et al. | 55/16 |
| 4,963,165 | 10/1990 | Blume et al. | 53/22 |
| 4,994,094 | 2/1991 | Behling et al. | 55/16 |
| 5,032,148 | 7/1991 | Baker et al. | 55/16 |
| 5,069,686 | 12/1991 | Baker et al. | 55/16 |
| 5,127,926 | 7/1992 | Baker et al. | 55/16 |
| 5,952,523 | 9/1999 | Papavassiliou et al. | 560/241.1 |

*Primary Examiner*—Gary Geist
*Assistant Examiner*—Taylor V. Oh
*Attorney, Agent, or Firm*—J. Farrant

[57] ABSTRACT

A process and apparatus for vinyl acetate production. A membrane unit containing a membrane selectively permeable to ethylene over argon is used to recover ethylene from the argon purge stream.

38 Claims, 5 Drawing Sheets

MEMBRANE PROCESS FOR ARGON PURGING FROM VINYL ACETATE REACTORS

This is a continuation-in-part application of application Ser. No. 08/890,856, filed Jul. 10, 1997, now U.S. Pat. No. 5,817,841.

FIELD OF THE INVENTION

The invention relates to manufacture of vinyl acetate in a reactor, and in particular to using a membrane unit to treat off-gas streams from the reactor to purge argon and other inert gases without losing large amounts of ethylene reagent.

BACKGROUND OF THE INVENTION

A large number of chemical intermediates are produced by catalytic oxidation of an appropriate hydrocarbon feedstock. One of the most important intermediates produced in this manner is vinyl acetate, which is made by oxidation of ethylene and acetic acid in the presence of a platinum group metal catalyst. The process operates in a loop, with modest conversion per pass, so that large amounts of ethylene are recirculated back to the reactor at each pass. The raw gas from the reactor is usually scrubbed with water to remove the product before the gas is recirculated.

Vinyl acetate manufacturing is well known in the art, and is discussed, for example, in U.S. Pat. No. 3,444,189, to Union Oil Co., which describes the synthesis of vinyl acetate by oxidation of ethylene and acetic acid. Other references that teach the general manufacturing process for vinyl acetate include U.S. Pat. No. 3,557,191, to DuPont, which describes a process that uses ethylene to produce acetic acid, which is then reacted with additional ethylene to produce vinyl acetate. U.S. Pat. No. 3,547,983, to Air Reduction Co., Inc., describes the use of ethane instead of ethylene in the production of vinyl acetate.

Many oxidation processes were originally developed using air as the oxygen source, but modern processes frequently operate with a feed of oxygen-enriched air or high-purity oxygen. The use of pure oxygen typically increases yields and reduces or eliminates the need for nitrogen purging from the process loop, since much less inert gas is fed into the loop initially.

Even when oxygen-oxidation is used, however, some purging is necessary. This is because "pure" oxygen is typically slightly less than 100% pure. The most significant other component is argon, with a typical concentration of about 1%. Argon is present in air and, since argon and oxygen have close boiling points, is not well separated in the cryogenic distillation process used to produce oxygen from air.

If argon is not removed, it builds up in the reactor loop, and can adversely affect the reaction dynamics and the flammability of the gas mixture, and/or reduce the life of the catalyst. Therefore, current vinyl acetate production processes normally provide for a small purge stream to be withdrawn from the loop, usually after the vinyl acetate product has been scrubbed out. In addition to argon, the purge gas typically contains unreacted ethylene and oxygen, carbon dioxide, nitrogen, small amounts of methane, ethane and/or propane, and other contaminants such as carbon monoxide, unreacted acetic acid, and water vapor. In prior art processes, this stream is incinerated or used as boiler fuel.

Although the volume of the purge stream is small, its destruction results in the loss, from a typical plant, of about 20 lb of ethylene for every tonne of vinyl acetate produced. At current estimated worldwide annual production of about 4 million tonnes, this represents a feedstock loss of about 40,000 tonnes annually. In a large-scale process of this type, even incremental improvements in efficiency can affect process economics significantly. Therefore, a process that can reduce or eliminate this loss of ethylene feedstock would be valuable to the industry.

Separation of certain gas mixtures by means of selective membranes has been known to be possible for many years, and membrane-based gas separation systems are emerging to challenge conventional separations technology in a number of areas. That membranes have the potential to separate organic vapors from other gases is also known. For example, U.S. Pat. Nos. 4,553,983; 4,857,078; 4,963,165; 4,906,256; 4,994,094; 5,032,148; 5,069,686; 5,127,926; 5,281,255 and 5,501,722 all describe membranes, systems or processes suitable for such separations.

U.S. Pat. No. 4,879,396, to Ozero, discloses a process for removing both carbon dioxide and argon from an ethylene oxide reactor loop by means of an argon-selective membrane, that is, a membrane that preferentially permeates argon and retains ethylene. U.S. Pat. No. 4,904,807, also to Ozero, discloses a process for removing argon from the reactor loop by means of an argon-selective membrane. In both cases, because the membrane is not perfectly selective, a portion of the ethylene is lost inevitably with the argon vent stream.

SUMMARY OF THE INVENTION

The invention is a process and apparatus for producing vinyl acetate that provides a new and advantageous technique for venting excess argon and other contaminants from the reaction loop with reduced loss of ethylene.

In its basic form, the process of the invention comprises:
(a) reacting ethylene, acetic acid, and oxygen in a reaction zone to form vinyl acetate;
(b) withdrawing from the reaction zone a crude product stream comprising vinyl acetate, ethylene and argon;
(c) removing at least a portion of the crude product stream to form a non-product stream;
(d) providing a membrane having a feed side and a permeate side, and being selectively permeable to ethylene over argon;
(e) passing at least a portion of the non-product stream across the feed side under conditions in which there is a pressure drop from the feed side to the permeate side;
(f) withdrawing from the feed side an argon-rich purge stream enriched in argon and depleted in ethylene compared with the non-product stream;
(g) withdrawing from the permeate side an ethylene-rich permeate stream enriched in ethylene and depleted in argon compared with the non-product stream;
(h) recirculating at least a portion of the ethylene-rich permeate stream to the reaction zone.

Step (a), the reaction of ethylene, acetic acid, and oxygen to form vinyl acetate may be carried out in any known manner, such as by using an oxygen-oxidation process in the presence of a platinum group metal catalyst, preferably a palladium salt, such as palladium chloride. The reaction may be carried out in a single-stage reactor or in a multiple-stage reactor. Depending on the specifics of the reaction process used, the gas mixture withdrawn from the reactor typically contains vinyl acetate, ethylene, oxygen, ethane, carbon dioxide, nitrogen, methane, argon, water vapor and minor amounts of other components. In some oxygen-oxidation plants, methane is added to raise the flammability limit of the feed gas and can be present in the off-gas.

The crude vinyl acetate product may be removed from the raw gas exiting the reactor, as specified in step (c), by any convenient technique. The standard procedure in the industry is to absorb the vinyl acetate into water, leaving a scrubbed gas stream. In prior art processes, a small amount of this scrubbed gas stream is purged to remove argon and other contaminants, as explained in the Background section above. The remainder, or at least a portion of the remainder, is further treated to remove carbon dioxide, and then recirculated to the reactor.

In the process of the invention, a portion of the scrubbed non-product gas stream is passed to a membrane unit. The unit contains a membrane, preferably a rubbery membrane, that is selectively permeable to ethylene compared with argon; that is, it permeates ethylene faster than argon. The membrane separation process may be configured in many ways, and may include a single bank of membrane modules or an array of two or more banks in multi-stage or multi-step arrangements.

A driving force for permeation across the membrane is usually provided by maintaining a pressure difference between the feed and permeate sides. This can be accomplished in a variety of ways.

Since the membrane is selectively permeable to ethylene, the residue stream leaving the feed side of the membrane is enriched in argon and depleted in ethylene compared with the feed stream to the membrane. It is possible to remove from the membrane feed stream, that is, to recover into the membrane permeate stream, a chosen percentage, such as 30%, 40%, 50%, 60%, 70%, 80%, 90%, 95% or even 99% of the ethylene that would otherwise be vented and lost.

As in prior art processes, carbon dioxide as well as argon must be removed from the reactor off-gas to control build-up in the reactor. This may be done by any convenient method. The carbon dioxide removal step may be carried out on a separate portion of the scrubbed, non-product gas stream, may be carried out on the permeate stream following the removal of argon by the membrane separation step, or may be carried out upstream of the membrane separation step, for example. This flexibility represents a further advantage of the invention. Since it is generally, although not necessarily, the case that the ethylene-enriched stream will be returned to the reactor loop, this recirculation of part of a stream that was previously vented from the loop can be used to adjust the reaction characteristics to some extent.

In another aspect, the invention is apparatus for vinyl acetate manufacture, including a reactor, a vinyl acetate recovery and purification train, a carbon dioxide removal unit and a membrane unit, containing a membrane selectively permeable to ethylene over argon, for argon removal.

In yet another aspect, the invention is a process for treating an argon purge stream to vent argon and recapture ethylene.

It is an object of the invention to improve vinyl acetate manufacturing processes.

It is an object of the invention to provide a process for removing argon from vinyl acetate reactor vent streams.

It is an object of the invention to provide a process for removing argon from vinyl acetate reactor vent streams with minimal corresponding loss of ethylene.

Other objects and advantages of the invention will be apparent from the description of the invention to those of ordinary skill in the art.

DETAILED DESCRIPTION OF THE INVENTION

Figure 1:
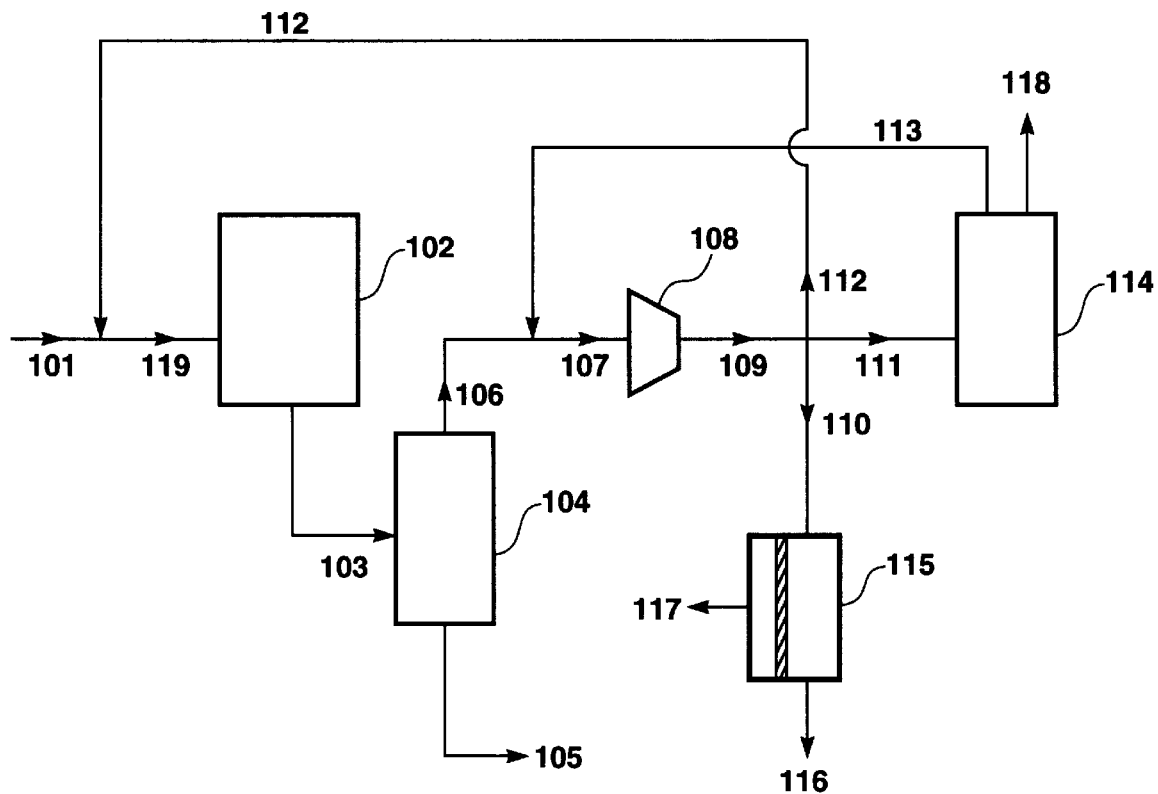
FIG. 1 is a schematic diagram of the basic embodiment of the invention.

The term stage-cut as used herein means the ratio of the membrane permeate volume flow to the membrane feed volume flow.

The term rubbery as used herein means rubbery or elastomeric.

The terms two-step and multi-step mean an arrangement of membrane modules or banks of modules connected together such that the residue stream from one module or bank of modules becomes the feedstream for the next.

The term two-stage and multi-stage mean an arrangement of membrane modules or banks of modules connected together such that the permeate stream from one module or bank of modules becomes the feedstream for the next.

The term membrane array means a set of membrane modules or banks of modules connected in a multi-step arrangement, a multi-stage arrangement, or mixtures or combinations of these.

The term product residue stream means the residue stream exiting a membrane array when the membrane separation process is complete. This stream may be derived from one membrane bank, or may be the pooled residue streams from several membrane banks.

The term product permeate stream means the permeate stream exiting a membrane array when the membrane separation process is complete. This stream may be derived from one membrane bank, or may be the pooled permeate streams from several membrane banks.

All percentages cited herein are by volume unless specifically stated otherwise.

In a basic embodiment, the process of the invention includes the following steps:

1. Reaction of ethylene, acetic acid, and oxygen to make vinyl acetate.

2. Treatment of gas exiting the reactor to separate vinyl acetate, and subsequent recovery of vinyl acetate product.

3. Argon removal from the reactor recirculation loop.

4. Carbon dioxide removal from the reactor recirculation loop.

5. Recirculation of unreacted reagents to the reactor.

In the process of the invention, steps 1 and 2, reaction and vinyl acetate separation, can be carried out by any known techniques, as described in the Background section above. Vinyl acetate is formed from ethylene, acetic acid, and oxygen by the reaction:

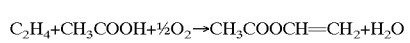

Modern reactors perform this reaction in the vapor phase and in the presence of a palladium salt catalyst at temperatures typically about 200° C. and pressures typically about 150 psia. In an oxygen-oxidation process, the reaction is preferably accomplished in one stage, as this will generally result in higher conversion of ethylene and acetic acid to vinyl acetate. The crude product is then separated, and the gas exiting the separation unit can be split into a direct recycle stream and into a portion or portions that are sent for inerts removal.

Older reactors that use air as the oxidizing agent are also within the scope of the invention. More discussion of typical process configurations for air-oxidation reactors is included in parent application serial number 08/890,856, now U.S. Pat. No. 5,817,841, which is incorporated herein by reference in its entirety.

The reactors themselves may be of any kind that provide for good contact between reagents and catalyst and for good temperature control and removal of waste heat. Shell and tube reactors, with the catalyst on the inner surfaces of the tubes and a coolant, such as water, flowing on the shell side, are preferred.

The exact composition of the reaction mixture may be varied in conjunction with pressure, temperature and flow rate to provide a desired overall yield, efficiency per pass and so on, as is known in the art. As a guideline, the feed to the reactor will typically contain 10–20 wt % oxygen, 20–40 wt % ethylene, and 40–80 wt % acetic acid.

The reaction may be carried out at pressures up to 1,000 psia or even higher. However, very high pressures are not generally necessary and a pressure in the range 50–150 psia is preferred. The preferred operating temperatures are in the range 100–250° C., and a temperature of around 175–200° C. is most preferred.

Separation and recovery of the crude vinyl acetate gas exiting the reactor can be performed by any known method. For example, the raw gas can be passed into a scrubbing column and run counter-current to a water stream. Vinyl acetate is readily absorbed into the water to form a dilute aqueous solution. The solution can then be passed to a recovery train, including, for example, one or more flash vessels, stripping columns, and distillation units, such as is known in the art, for purification and retrieval of the vinyl acetate product.

Steps 3 and 4, purging of argon and carbon dioxide from the reactor loop, represent an important aspect of the invention. In particular, the manner in which the argon purging is carried out differs from the prior art.

As was mentioned in the Background section above, current processes withdraw a stream of sufficient volume to maintain an acceptable argon concentration in the main recycle loop, and burn this stream as fuel or simply incinerate it. Since this stream often contains up to ten or more times as much ethylene as argon, this means that up to ten moles of ethylene may be lost for every mole of argon that is purged. The processes of the invention, on the other hand, are able to recover and recirculate significant amounts, typically 30% or more, such as 40%, 50%, 60%, 70%, 80%, 90%, 95% or even more of the ethylene content of this argon purge stream. That is, as a specific example, if the argon purge stream contains ten moles of ethylene per mole of argon, use of the process of the invention can reduce the ethylene loss from ten moles/mole of argon to 7 moles/mole of argon, 6 moles/mole of argon, 5 moles/mole of argon, 4 moles/mole of argon, 3 moles/mole of argon, 2 moles/mole of argon, 1 mole/mole of argon, 0.5 moles/mole of argon or even less.

Various process configurations for achieving this result are possible within the scope of the invention. FIGS. 1–5 show representative, but non-limiting, embodiments of the invention. It will be appreciated by those of skill in the art that these are very simple schematic diagrams, intended to make clear the key aspects of the invention, and that an actual process train will usually include many additional components of a standard type, such as heaters, chillers, condensers, pumps, blowers, other types of separation and/ or fractionation equipment, valves, switches, controllers, pressure-, temperature-, level- and flow-measuring devices and the like.

Turning now to FIG. 1, the raw feed stream, 101, containing ethylene, acetic acid, and oxygen is mixed with recirculating gas 112 to form combined reactor feed stream 119, which enters the reactor, 102. Gas containing the crude vinyl acetate product exits the reactor as stream 103, and passes to the vinyl acetate recovery and purification train, depicted overall as unit 104. The vinyl acetate product is withdrawn as stream 105.

A non-product gaseous overhead stream, 106, from the vinyl acetate recovery train contains a mixture of ethylene, oxygen, carbon dioxide, nitrogen, argon, ethane and trace amounts of other gases. Typical values for a stream from a vinyl acetate recovery unit are in the range up to 60–70% or more ethylene, up to 5% oxygen, 10–20% carbon dioxide, 5–10% nitrogen, 5–10% argon and up to 10% ethane/methane. However, the composition can vary over a broad range, depending on the specific reactor, catalyst, and pressure and temperature conditions of the reactor. This stream is mixed with the carbon-dioxide-depleted stream 113, and the combined stream, 107, is recompressed in compressor 108. Compressed stream 109 is split into three portions: stream 112, which is recirculated directly to the reactor; stream 111, which forms the feed stream to the carbon dioxide removal unit; and stream 110, which forms the feed stream to the argon removal unit.

It will be apparent to those of skill in the art that the relative sizes of stream 110, 111, and 112 are selected to maintain the desired concentration of carbon dioxide and argon in the reactor gas mix in accordance with plant specifications, and can be adjusted as necessary. As just one example, about half of the absorber overhead stream 109 might be recirculated directly, and the remaining half split about equally between the carbon dioxide removal system and the argon removal system. Typically, however, the feed stream, 110, to the argon removal system will be comparatively small, such as only 1%, 2%, 5% or 10% of stream 109.

Stream 111 is treated to remove excess carbon dioxide by any known method, depicted overall as unit 114 in the figure. Stream 113, depleted in carbon dioxide, is recirculated upstream of compressor 108. Carbon dioxide is vented via line 118.

Stream 110 is treated to remove excess argon. This is achieved by passing stream 110 across the feed side of membrane unit 115.

A synthetic polymer membrane separates the components of a gas or vapor mixture because the components permeate the membrane at different rates. The permeability, $P$ [$cm^3$ (STP)·cm/$cm^2$·s·cmHg], of a polymer membrane material for a gas is defined as the rate at which that gas moves through a standard thickness [1 cm] of the material under a standard driving force [a pressure difference of 1 cmHg].

A measure of the ability of a membrane to separate two gases is the selectivity, $\alpha$, defined as the ratio of the gas permeabilities, $P_2/P_2$. The intrinsic selectivity of a polymer material is established by measuring the permeabilities with pure gas or vapor samples, then calculating the ratio. The actual selectivity obtained in a real separation process is established by making permeation measurements with gas mixtures. Selectivity can also be expressed as:

$$\alpha = \frac{D_1}{D_2} \cdot \frac{k_1}{k_2}$$

where D is the diffusion coefficient of the gas in the membrane [$cm^2/s$], which is a measure of the gas mobility, and k is the Henry's law sorption coefficient, which links the concentration of the gas in the membrane material to the pressure in the adjacent gas [$cm^3(STP)/cm^3 \cdot cmHg$], and is a measure of the gas solubility in the membrane material.

The ratio $D_1/D_2$ is the ratio of the diffusion coefficients of the two gases and can be viewed as the mobility selectivity, reflecting the different sizes of the two molecules. The ratio $k_1/k_2$ is the ratio of the Henry's law coefficients of the two gases and can be viewed as the solubility selectivity, reflecting the relative condensabilities of the two gases.

In all polymer materials, the diffusion coefficient decreases with increasing molecular size. Hence, the diffusion component of the selectivity always favors the passage of small molecules over large ones. The diffusion coefficient thus favors permeation of argon over ethylene. The solubility component of the selectivity, on the other hand, is a measure of the energy required for sorption and normally increases with molecular diameter, because larger molecules are normally more condensable than smaller ones. The solubility coefficient favors permeation of ethylene over argon, therefore. The relative contribution of the diffusion and solubility coefficients determines the overall selectivity of a membrane material.

The balance between diffusion selectivity and solubility selectivity is different for glassy and rubbery polymers. In rubbery polymers, the solubility term is usually the dominant term, so that rubbery membranes are selective for larger, more condensable molecules over smaller, less condensable molecules. Furthermore, since the polymer chains in rubbery membranes are more flexible than in glassy membranes, the fluxes of all permeants, whether the more or less favored permeant, are generally higher through rubbery membranes than through glassy membranes.

In the case of separation of argon from ethylene, both components have fairly small molecules and both have very low boiling points and are not easily condensed. The smaller molecular size of argon means that glassy materials slightly favor the passage of argon over ethylene. The relative condensability of ethylene means that rubbery materials slightly favor the passage of ethylene over argon. However, whether glassy or rubbery membrane materials are used to separate the components, the selectivity is relatively low. For example, polyimides and similar glassy materials have a selectivity for argon over ethylene of up to about 4, and silicone rubber and similar rubbery materials have a similar selectivity of about 4 for ethylene over argon.

It might be supposed, therefore, that it is simply a matter of choice and convenience which type of membrane to use, and that essentially equivalent results will be obtained in either case. This, however, is not so, as we have shown. The difference in performance that can be achieved arises in part from the difference in stage-cuts needed to optimize the membrane separation, depending on whether the residue or the permeate stream is the vented stream. Stage-cut is defined as the ratio of total permeate flow to total feed flow, and is typically expressed as a percentage. For example, a stage-cut of 20% means that of 100 volumes of feed gas, 20 volumes pass to the permeate side and 80 volumes remain on the feed side.

When an ethylene-selective membrane is used, as is taught herein, the argon-enriched purge vent stream is the residue stream. In this case, at low stage-cuts, comparatively little removal of ethylene from the feed stream will have been achieved, and if the residue stream is vented at this point, comparatively large amounts of ethylene will be lost. As the stage-cut increases, a higher proportion of the ethylene passes into the permeate stream, and the higher the stage-cut, the less ethylene will be left in the residue stream. Thus recapture of any amount of ethylene is possible, at least theoretically, by an appropriately high choice of stage-cut. Of course, membrane area required to perform the separation scales in proportion to stage-cut, which will impose a practical limit on ethylene recovery.

Because the membrane does not make a perfect separation, some ethane, argon and other undesirable components will permeate along with the ethylene and be recycled to the reactor loop. The high stage-cuts that permit recovery of large amounts of ethylene may also allow unacceptable amounts of these undesirable components to be recycled. In some cases, therefore, these compounds may need to be purged at the same rate (lb/h) as would be purged absent the membrane system. Achieving a constant purge rate of one or more components may require a lower stage-cut than might be chosen for maximum ethylene recovery. Thus, plant operators must decide between the trade-off of high ethylene recovery, and the lower ethylene recovery that results from ensuring the desired rate of contaminant removal. The Examples section below compares some typical ethylene recoveries that can be achieved when the process of the invention is configured either for maximum ethylene recovery or for a constant contaminant purge rate.

Those of skill in the art will appreciate that the stage-cut used will also vary with the specific feed composition, membrane performance and system operating conditions. As a guideline, when dealing with typical vinyl acetate recovery unit overhead streams, for example containing no more than about 70% ethylene and no more than about 10% argon, it is preferred to operate at a stage-cut of at least about 30%, more preferably at least about 40%, and most preferably at least about 50%. It is expected that stage-cuts of 60%, 70%, 80% or even 90% or more may be used in some cases.

Returning to FIG. 1, membrane unit 115 contains ethylene-selective membranes, which generally means rubbery or elastomeric membranes. Examples of polymers that can be used to make elastomeric membranes, include, but are not limited to, nitrile rubber, neoprene, polydimethylsiloxane (silicone rubber), chlorosulfonated polyethylene, polysilicone-carbonate copolymers, fluoroelastomers, plasticized polyvinylchloride, polyurethane, cis-polybutadiene, cispolyisoprene, poly(butene-1), polystyrene-butadiene copolymers, styrene/butadiene/styrene block copolymers, styrene/ethylene/butylene block copolymers, thermoplastic polyolefin elastomers, and block copolymers of polyethers, polyamides and polyesters. The preferred membrane material is silicone rubber, since silicone rubber membranes are already in commercial production and use for other separations.

As an alternative to a rubbery ethylene-selective membrane, ethylene-selective membranes can also be made from super-glassy materials, such as poly(trimethylsilylpropyne) [PTMSP] and the like, the general use of which is described in U.S. Pat. No. 5,281,255, for example. As yet another alternative, finely microporous inorganic membranes, such as the adsorbent carbon membranes described in U.S. Pat. No. 5,332,424, the pyrolysed carbon membranes described in U.S. Pat. No. 4,685,940, or certain ceramic membranes may be used. These alternatives, most of which exhibit acceptable ethylene selectivity only in the presence of a $C_{3+}$ hydrocarbon or other relatively condensable molecule in the gas mix, and most of which are less readily available than rubbery polymer membranes, are less preferred, but may be useful in some circumstances. Membranes comprising immobilized liquid films can also be used. However, these membranes tend to be unstable over long periods of time, and therefore are less preferred.

The membrane may take the form of a single homogeneous layer, an integral asymmetric membrane, a multilayer composite membrane, a membrane incorporating a gel or liquid layer or particulates, or any other form known in the art. Composite membranes, in which the elastomeric selective membrane layer is supported on a mechanically strong, highly permeable support layer, are preferred.

The membranes may be manufactured as flat sheets or as fibers and housed in any convenient module form, including spiral-wound modules, plate-and-frame modules and potted hollow-fiber modules. The making of all these types of membranes and modules is well known in the art. Flat-sheet membranes in spiral-wound modules are our most preferred choice.

Membrane unit 115 may contain a single membrane module or bank of modules or an array of modules. A single-stage membrane separation operation is adequate for many applications. If the residue stream requires further purification, it may be passed to a second bank of modules for a second processing step. If the permeate stream requires further concentration, it may be passed to a second bank of modules for a second-stage treatment. Such multistage or multistep processes, and variants thereof, will be familiar to those of skill in the art, who will appreciate that the membrane separation step may be configured in many possible ways, including single-stage, multistage, multistep, or more complicated arrays of two or more units in series or cascade arrangements. If an array of membranes is used, the stage-cut preferences cited above for obtaining good ethylene recovery refer to the overall stage-cut of the array. In other words, the stage-cut is the ratio of total product permeate stream flow to raw feed flow to the first membrane bank in the array.

A pressure difference between the feed and permeate sides of the membrane is used to provide a driving force for transmembrane permeation. Vinyl acetate reactors are usually run at pressures above atmospheric, such as about 100–300 psia, and the off-gas from the vinyl acetate recovery unit is recompressed to reactor pressure by compressor 108 for recirculation. Thus, it is normally possible, and is preferred, to operate the membrane system at the feed pressure available from the reactor recompressor without additional compression. If it is desired to increase the pressure difference across the membrane, this can be done by passing the membrane feed stream 110 through an additional compressor or by lowering the pressure on the permeate side by means of a vacuum pump, for example.

The membrane unit separates the feed stream 110 into permeate stream 117 and residue stream 116. The argon-enriched residue stream is vented from the process to any appropriate destination. For a typical stream, the residue stream will be slightly enriched in methane content compared with the membrane feed stream. Therefore, as in prior art processes, the vent stream may be incinerated or used as fuel. However, in the process of the invention, this will result in a much smaller loss of ethylene than was previously possible. By following the teachings given herein, it is possible to reduce the ethylene loss per mole of argon vented by as much as 50%, 60%, 70%, 80%, 90%, or even more.

Permeate stream 117, now depleted of argon and enriched in ethylene content, is withdrawn. The ultimate destination of the recovered ethylene is the main reactor. A number of options exist for the method of ethylene recycle, as discussed below and shown schematically in FIGS. 2–4.

Figure 2:
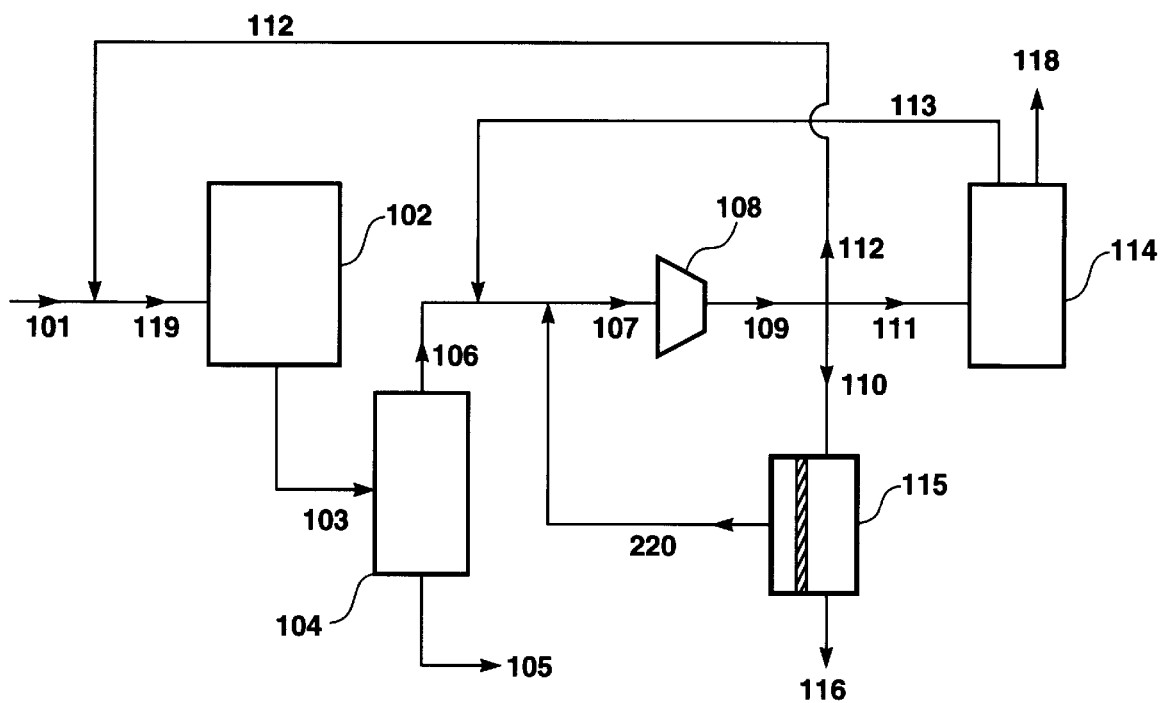
FIG. 2 is a schematic diagram of an alternative embodiment of the invention in which the membrane permeate is recycled to the main reactor loop.

One alternative embodiment is shown schematically in FIG. 2, in which like elements are numbered as in FIG. 1. In this figure, the permeate stream, 220, is returned to the main recycle loop by recirculating it upstream of compressor 108. This embodiment makes use of the excess horsepower available from compressor 108, thus involves no additional capital expense or maintenance.

Figure 3:
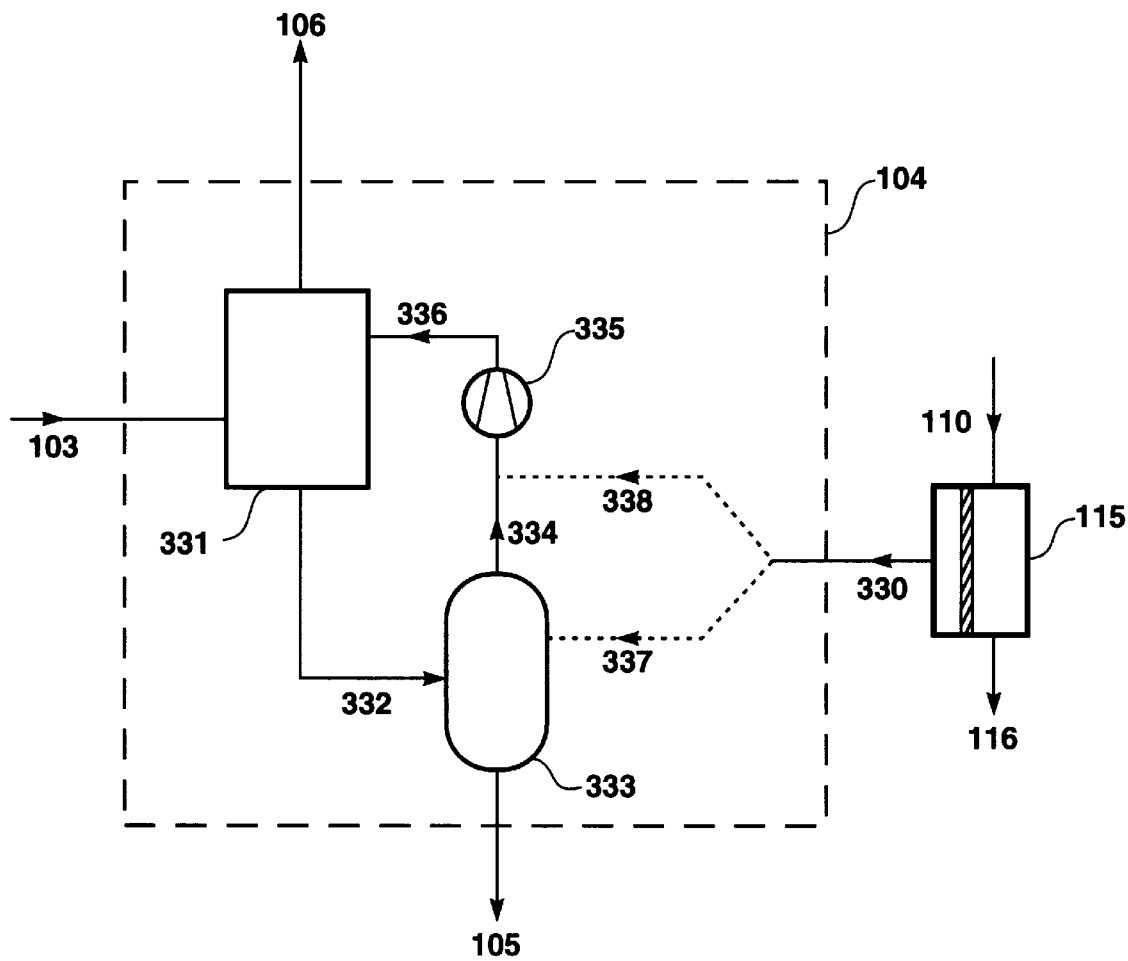
FIG. 3 is a schematic drawing of an embodiment of the vinyl acetate recovery and purification unit of FIG. 1 in more detail.

Alternatively, the permeate can be returned to some point in the vinyl acetate recovery and purification train, as shown schematically in FIG. 3, in which like elements are numbered as in FIG. 1. FIG. 3 shows vinyl acetate recovery and purification train 104, indicated by the dashed outline, broken down in more detail. Crude vinyl acetate stream 103 is scrubbed in absorber 331, then sent to a flash or distillation vessel or series of vessels, indicated overall as unit 333. Vinyl acetate product is withdrawn as stream 105. Gaseous overhead stream 334 is compressed in compressor 335, and compressed stream 336 is fed back to absorber 331. Permeate stream 330 could be passed directly to unit 333, as indicated by dotted line 337, or could be added to gaseous overhead stream 334 upstream of compressor 335, as indicated by dotted line 338. This embodiment also takes advantage of the excess horsepower available from an existing compressor in the process loop.

Figure 4:
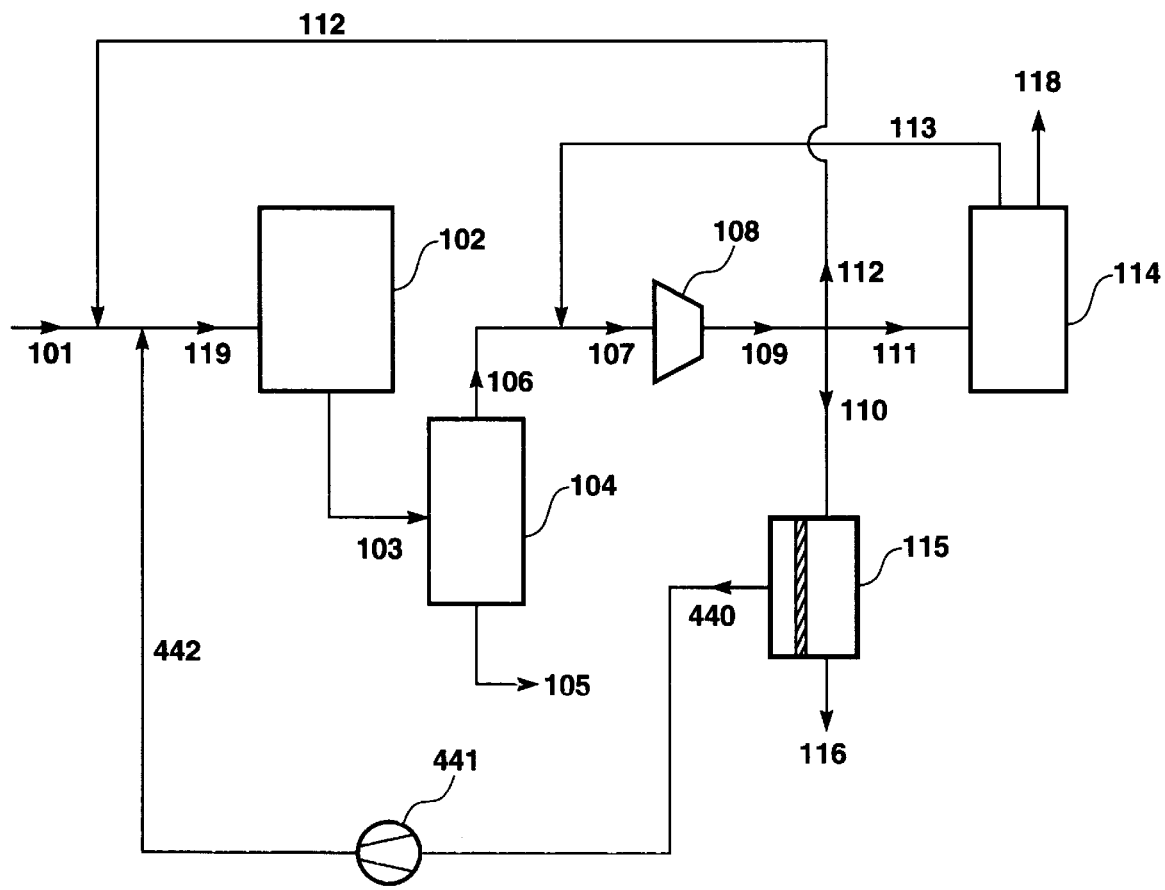
FIG. 4 is a schematic diagram of an alternative embodiment of the invention in which the membrane permeate is recycled directly to the reactor.

The permeate stream can also be recycled directly back to the reactor, as shown schematically in FIG. 4, in which like elements are numbered as in FIG. 1. Turning now to FIG. 4, permeate stream 440 is recompressed to reactor pressure in compressor 441. Compressed stream 442 passes to the feed stream along with recycle stream 112 to form combined reactor feed stream 119. This recycle method requires that an additional compressor be added to the existing plant, but can provide a large quantity of argon-depleted ethylene to be added directly to the reactor feed stream.

Figure 5:
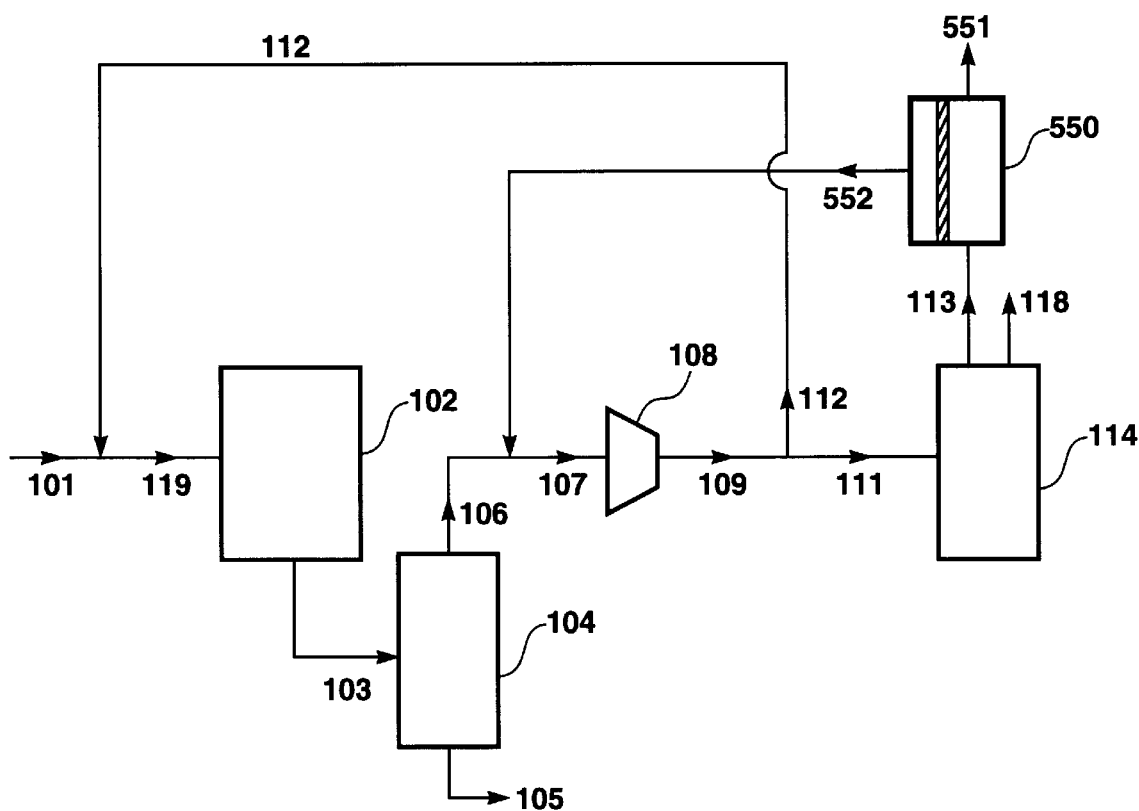
FIG. 5 is a schematic diagram of an alternative embodiment of the invention in which the carbon dioxide removal step and the argon removal step are carried out in series.

Yet another alternative embodiment, in which the carbon dioxide and argon removal operations are carried out in series, is shown schematically in FIG. 5, in which like elements are numbered as in FIG. 1. In FIG. 5, compressed overhead stream 109 is split into two portions, with one portion, stream 112, being recycled directly to the reactor feed stream. The other portion, stream 111, passes to carbon dioxide removal unit 114. Carbon-dioxide-depleted stream 113 exits the top of unit 114. This stream forms the feed to membrane unit 550. Ethylene-depleted residue stream 551 is discharged. Permeate stream 552, enriched in ethylene and depleted in carbon dioxide, is recycled upstream of compressor 108 for recirculation in the main reactor loop. Although the entirety of stream 113 is shown being passed to the membrane unit, it will be apparent to those of skill in the art that any fraction of stream 113 may be treated in the membrane unit, with the remainder of the stream being recycled to the reactor loop without argon-removal treatment. The amount of stream 113 to be passed to the membrane unit can be determined based on flow rates, efficiency per pass and so on, in accordance with plant specifications, and can be adjusted as necessary.

Based on the descriptions of FIGS. 1–5, those of skill in the art will appreciate that various other configurations are possible within the scope of the invention. As one example, stream 220 of FIG. 2 can be subjected to carbon dioxide removal treatment before recirculation. As another example, the argon removal membrane system can be positioned in series before the carbon dioxide removal treatment. That is, the apparatus arrangement shown in FIG. 5 can be reversed, so that membrane unit 550 is installed in line 111, or on a bypass line parallel to line 111, upstream of the carbon dioxide removal unit.

Thus, the scope of the invention is not limited to any specific configuration but to the use of an ethylene-selective membrane to provide improved argon-purging capability.

In another aspect, the invention is apparatus useful for vinyl acetate manufacture. In this aspect, the invention includes the following elements:

(a) a reactor for reacting ethylene, acetic acid and oxygen;

(b) an vinyl acetate recovery and purification unit connected to the reactor so that gas can pass from the reactor into the vinyl acetate recovery unit;

(c) a carbon dioxide removal unit connected to the vinyl acetate recovery unit;

(d) a membrane unit containing a membrane selectively permeable to ethylene over argon and connected to the vinyl acetate recovery unit;

(e) one or more lines for recirculating gases from the vinyl acetate recovery unit, the carbon dioxide removal unit and the membrane unit to the reactor.

As was discussed with regard to the process embodiments, many variations in the specific configuration are possible. For example, with reference to FIG. 2, 102 is the reactor; 104 forms the vinyl acetate recovery and purification unit; 114 forms the carbon dioxide removal unit; the membrane unit is 115; and lines 112, 113, and 220 are lines for recirculating gases.

With reference to FIG. 5, 102 is the reactor; 104 forms the vinyl acetate recovery and purification unit; 114 forms the carbon dioxide removal unit; the membrane unit is 550; and lines 112 and 552 are lines for recirculating gases. In this case, the connection of the membrane unit to the vinyl acetate recovery unit is indirect, through the carbon dioxide removal unit.

In yet another aspect, the invention is a process for treating an argon purge stream to vent argon and recapture ethylene in a vinyl acetate manufacturing process. In this aspect, the invention comprises:

(a) providing a membrane having a feed side and a permeate side, and being selectively permeable to ethylene over argon;

(b) passing at least a portion of the purge stream across the feed side under conditions in which there is a pressure drop from the feed side to the permeate side;

(c) withdrawing from the feed side an argon-rich stream enriched in argon and depleted in ethylene compared with the purge stream;

(d) withdrawing from the permeate side an ethylene-rich permeate stream enriched in ethylene and depleted in argon compared with the purge stream;

(e) recirculating at least a portion of the ethylene-rich permeate stream to the vinyl acetate manufacturing process.

The invention is now illustrated in further detail by specific examples. These examples are intended to further clarify the invention, and are not intended to limit the scope in any way.

EXAMPLES

Example 1

Permeation Properties of Silicone Rubber Membrane Stamps

A microporous support membrane was dip-coated in a 6% dimethyl siloxane solution at 1 ft/min coating speed, then dried in an oven at 60° C. to crosslink the membrane. The resulting membranes had a nominal selective layer thickness of 2.7 $\mu$m. Samples of the finished composite membrane were cut into 12.6 cm$^2$ stamps and tested in a permeation test-cell apparatus with pure oxygen, nitrogen, argon, methane, ethylene, and carbon dioxide at 23° C. feed temperature, 50 psig feed pressure, and ambient permeate pressure. The gas fluxes of the membranes were measured, and the selectivities were calculated. The results of the tests are shown in Table 1. Any membrane with a selectivity less than the intrinsic selectivity of the material was considered defective.

TABLE 1

| Gas | Flux × 10$^{-6}$ cm$^3$(STP)/cm$^2$ · sec · cmHg | Gas/Nitrogen Selectivity (–) |
|---|---|---|
| Nitrogen | 105 | — |
| Oxygen | 228 | 2.2 |
| Argon | 236 | 2.2 |
| Methane | 348 | 3.3 |
| Ethane | 800 | 7.6 |
| Ethylene | 983 | 9.4 |
| Carbon Dioxide | 1,360 | 13.0 |

Examples 2–6

Ethylene Recovery as a Function of Stage-Cut

Example 2

A series of computer calculations were performed with a modeling program, ChemCad III (ChemStations, Inc., Houston, Tex.), to illustrate the effect of stage-cut on an ethylene/argon separation process using an ethylene-selective membrane.

The feed mixture was chosen to approximate a vent stream from a vinyl acetate recovery unit, and was assumed to contain the following components in the concentrations noted:

| | |
|---|---|
| 70% | Ethylene |
| 3% | Oxygen |
| 7% | Argon |
| 5% | Nitrogen |
| 13% | Carbon Dioxide |
| 1% | Methane |
| 1% | Ethane |

We assumed membrane pressure-normalized fluxes as follows, which were determined in Example 1 for silicone rubber membranes:

| | |
|---|---|
| Ethylene | 983 × 10$^{-6}$ cm$^3$(STP)/cm$^2$ · sec · cmHg |
| Oxygen | 228 × 10$^{-6}$ cm$^3$(STP)/cm$^2$ · sec · cmHg |
| Argon | 236 × 10$^{-6}$ cm$^3$(STP)/cm$^2$ · sec · cmHg |
| Nitrogen | 105 × 10$^{-6}$ cm$^3$(STP)/cm$^2$ · sec · cmHg |
| Carbon Dioxide | 1,360 × 10$^{-6}$ cm$^3$(STP)/cm$^2$ · sec · cmHg |

-continued

| | |
|---|---|
| Methane | $348 \times 10^{-6}$ cm$^3$(STP)/cm$^2$ · sec · cmHg |
| Ethane | $800 \times 10^{-6}$ cm$^3$(STP)/cm$^2$ · sec · cmHg |

We assumed the one-stage membrane separation operation as in FIG. 1. In this Figure, line 110 carries the compressed overhead stream from the vinyl acetate recovery unit to membrane unit 115. The ethylene-enriched permeate stream is withdrawn through line 117. The ethylene-depleted, argon-enriched residue stream is withdrawn through line 116.

The stage-cut was assumed to be about 60%. The results of the calculations are shown in Table 2.

TABLE 2

| Component/Parameter | Stream 110 | Stream 116 | Stream 117 |
|---|---|---|---|
| Mass Flow Rate (lb/h) | 517.6 | 210.6 | 307.1 |
| Flow Rate (scfm) | 100 | 40.7 | 59.2 |
| Temperature (° C.) | 25 | 21 | 21 |
| Pressure (psia) | 115 | 115 | 20 |
| Component (mol %) | | | |
| Ethylene | 70.0 | 60.1 | 76.8 |
| Oxygen | 3.0 | 5.5 | 1.3 |
| Argon | 7.0 | 12.8 | 3.0 |
| Nitrogen | 5.0 | 10.7 | 1.1 |
| Carbon Dioxide | 13.0 | 8.3 | 16.2 |
| Methane | 1.0 | 1.6 | 0.6 |
| Ethane | 1.0 | 1.0 | 1.0 |
| Component (lb/h) | | | |
| Ethylene | 328.2 | 114.8 | 213.4 |
| Argon | 46.7 | 34.7 | 12.0 |

Membrane Area: 7 m$^2$

Example 3

Calculations were performed as in Example 2, except with a stage-cut of about 75%. The results of the calculations are shown in Table 3.

TABLE 3

| Component/Parameter | Stream 110 | Stream 116 | Stream 117 |
|---|---|---|---|
| Mass Flow Rate (lb/h) | 517.7 | 138.4 | 379.3 |
| Flow Rate (scfm) | 100 | 26.7 | 73.3 |
| Temperature (° C.) | 25 | 21 | 21 |
| Pressure (psia) | 115 | 115 | 20 |
| Component (mol %) | | | |
| Ethylene | 70.0 | 52.1 | 76.5 |
| Oxygen | 3.0 | 7.2 | 1.5 |
| Argon | 7.0 | 16.5 | 3.5 |
| Nitrogen | 5.0 | 15.2 | 1.3 |
| Carbon Dioxide | 13.0 | 6.1 | 15.5 |
| Methane | 1.0 | 1.9 | 0.7 |
| Ethane | 1.0 | 1.0 | 1.0 |
| Component (lb/h) | | | |
| Ethylene | 328.2 | 65.1 | 263.1 |
| Argon | 46.7 | 29.4 | 17.3 |

Membrane Area: 9 m$^2$

Example 4

Calculations were performed as in Example 2, except with a stage-cut of about 90%. The results of the calculation are shown in Table 4.

TABLE 4

| Component/Parameter | Stream 110 | Stream 116 | Stream 117 |
|---|---|---|---|
| Mass Flow Rate (lb/h) | 517.7 | 60.1 | 457.6 |
| Flow Rate (scfm) | 100 | 11.4 | 88.6 |
| Temperature (° C.) | 25 | 21 | 21 |
| Pressure (psia) | 115 | 115 | 20 |
| Component (mol %) | | | |
| Ethylene | 70.0 | 29.4 | 75.2 |
| Oxygen | 3.0 | 11.0 | 2.0 |
| Argon | 7.0 | 25.1 | 4.7 |
| Nitrogen | 5.0 | 29.0 | 1.9 |
| Carbon Dioxide | 13.0 | 2.4 | 14.4 |
| Methane | 1.0 | 2.4 | 0.8 |
| Ethane | 1.0 | 0.7 | 1.0 |
| Component (lb/h) | | | |
| Ethylene | 328.2 | 15.7 | 312.5 |
| Argon | 46.7 | 19.1 | 27.6 |

Membrane Area: 12 m$^2$

Example 5

Table 5, compiled from Tables 2, 3, and 4, compares the ethylene losses and the ethylene recovery rates of the process of the invention at varying stage-cuts. As can be seen, the higher the stage-cut, the lower is the ethylene loss in the argon vent stream, and the greater is the ethylene reovery.

TABLE 5

| Parameter | No membrane | Table 2 | Table 3 | Table 4 |
|---|---|---|---|---|
| Stage-Cut (%) | — | 60 | 75 | 90 |
| Membrane Area (m$^2$) | — | 7 | 9 | 12 |
| Ethylene concentration in vent stream (mol %) | 70.0 | 60.1 | 52.1 | 29.4 |
| Amount of Ethylene in vent stream (lb/h) | 328.2 | 114.8 | 65.1 | 15.7 |
| Moles of ethylene lost/mole of argon vented | 10 | 4.7 | 3.2 | 1.2 |
| Removal/Recovery compared to No membrane (%) | — | 65.0 | 80.2 | 95.2 |

Examples 6–9
Ethylene Recovery at Constant Level of Argon Purge

Example 6

A series of computer calculations were performed with a modeling program, ChemCad III (ChemStations, Inc., Houston, Tex.), to illustrate the ethylene recovery that can be achieved when a constant level of argon removal is required.

The feed composition and membrane pressure-normalized fluxes were assumed to be as in Example 2. The stage-cut was assumed to be about 60%. Also as in Example 2, it was assumed that, absent the membrane recovery unit, the process vents about 47 lb of argon and 328 lb of ethylene per hour. The membrane process was configured to maintain this same argon purge rate. The results of the calculations are shown in Table 6.

TABLE 6

| Component/Parameter | Stream 110 | Stream 116 | Stream 117 |
| --- | --- | --- | --- |
| Mass Flow Rate (lb/h) | 698.8 | 284.3 | 414.5 |
| Flow Rate (scfm) | 135.0 | 55.0 | 80.0 |
| Temperature (° C.) | 25 | 21 | 21 |
| Pressure (psia) | 115 | 115 | 20 |
| Component (mol %) | | | |
| Ethylene | 70.0 | 60.1 | 76.8 |
| Oxygen | 3.0 | 5.5 | 1.3 |
| Argon | 7.0 | 12.8 | 3.0 |
| Nitrogen | 5.0 | 10.7 | 1.1 |
| Carbon Dioxide | 13.0 | 8.3 | 16.2 |
| Methane | 1.0 | 1.6 | 0.6 |
| Ethane | 1.0 | 1.0 | 1.0 |
| Component (lb/h) | | | |
| Ethylene | 443.0 | 155.0 | 288.0 |
| Argon | 63.0 | 46.8 | 16.2 |

Membrane Area: 9.4 m$^2$

The process vents 155 lb/h of ethylene compared to the no-membrane case in which 328 lb/h of ethylene was vented. Thus, a stage-cut of 60% yields an ethylene recovery of about 50%.

Example 7

Calculations were performed as in Example 6, except with a stage-cut of about 75%, again configuring the membrane process for venting about 47 lb/h of argon. The results of the calculations are shown in Table 7.

TABLE 7

| Component/Parameter | Stream 110 | Stream 116 | Stream 117 |
| --- | --- | --- | --- |
| Mass Flow Rate (lb/h) | 823.1 | 220.0 | 603.1 |
| Flow Rate (scfm) | 159.0 | 42.4 | 116.6 |
| Temperature (° C.) | 25 | 21 | 21 |
| Pressure (psia) | 115 | 115 | 20 |
| Component (mol %) | | | |
| Ethylene | 70.0 | 52.1 | 76.5 |
| Oxygen | 3.0 | 7.2 | 1.5 |
| Argon | 7.0 | 16.5 | 3.5 |
| Nitrogen | 5.0 | 15.2 | 1.3 |
| Carbon Dioxide | 13.0 | 6.1 | 15.5 |
| Methane | 1.0 | 1.9 | 0.7 |
| Ethane | 1.0 | 1.0 | 1.0 |
| Component (lb/h) | | | |
| Ethylene | 521.8 | 103.5 | 418.3 |
| Argon | 74.3 | 46.8 | 27.5 |

Membrane Area: 14.2 m$^2$

In this case, the process vents about 105 lb/h of ethylene compared to the no-membrane case in which 328 lb/h of ethylene was vented. In other words, the ethylene recovery is nearly 70%.

Example 8

Calculations were performed as in Example 6, except with a stage-cut of about 90%, again configuring the membrane process for venting about 47 lb/h of argon. The results of the calculations are shown in Table 8.

TABLE 8

| Component/Parameter | Stream 110 | Stream 116 | Stream 117 |
| --- | --- | --- | --- |
| Mass Flow Rate (lb/h) | 1,268.3 | 147.3 | 1,121 |
| Flow Rate (scfm) | 245 | 27.9 | 217.1 |
| Temperature (° C.) | 25 | 21 | 21 |
| Pressure (psia) | 115 | 115 | 20 |
| Component (mol %) | | | |
| Ethylene | 70.0 | 29.4 | 75.2 |
| Oxygen | 3.0 | 11.0 | 2.0 |
| Argon | 7.0 | 25.1 | 4.7 |
| Nitrogen | 5.0 | 29.0 | 1.9 |
| Carbon Dioxide | 13.0 | 2.4 | 14.4 |
| Methane | 1.0 | 2.4 | 0.8 |
| Ethane | 1.0 | 0.7 | 1.0 |
| Component (lb/h) | | | |
| Ethylene | 804.0 | 38.5 | 765.5 |
| Argon | 114.5 | 46.7 | 67.8 |

Membrane Area: 28.7 m$^2$

In this case, the process vents only about 40 lb/h of ethylene compared to the no-membrane case in which 328 lb/h of ethylene was vented. This represents an ethylene recovery of about 90%.

Example 9

Table 9, compiled from Tables 6, 7, and 8, compares the ethylene losses and the ethylene recovery rates of the process of the invention at varying stage-cuts. As can be seen, the higher the stage-cut, the lower is the ethylene loss in the argon vent stream, and the greater is the ethylene recovery, while still maintaining the 47-lb/h argon purge rate.

TABLE 9

| Parameter | No membrane | Table 6 | Table 7 | Table 8 |
| --- | --- | --- | --- | --- |
| Stage-Cut (%) | — | 60 | 75 | 90 |
| Membrane Area (m$^2$) | — | 9.4 | 14.2 | 28.7 |
| Ethylene concentration in vent stream (mol %) | 70.0 | 60.1 | 52.1 | 29.4 |
| Amount of Ethylene in vent stream (lb/h) | 328.2 | 155.0 | 103.5 | 38.5 |
| Removal/Recovery compared to No membrane (%) | — | 52.8 | 68.5 | 88.3 |

The ethylene recovery rates shown in Table 9 are slightly lower than those shown in Table 5.

Examples 10–13

Ethylene Recovery as a Function of Stage-Cut

Example 10

A series of computer calculations were performed with a modeling program, ChemCad III (ChemStations, Inc., Houston, Tex.), as in Examples 2–6, to illustrate the effect of stage-cut on an ethylene/argon separation process using an ethylene-selective membrane.

In this set of calculations, the feed mixture was assumed to be leaner in ethylene and richer in carbon dioxide than in the previous examples, as noted below:

| | |
|---|---|
| 60% | Ethylene |
| 3% | Oxygen |
| 5% | Argon |
| 7% | Nitrogen |
| 20% | Carbon Dioxide |
| 2.5% | Methane |
| 2.5% | Ethane |

We assumed membrane pressure-normalized fluxes as follows, which were determined in Example 1 for silicone rubber membranes:

| | |
|---|---|
| Ethylene | $983 \times 10^{-6}$ cm$^3$(STP)/cm$^2 \cdot$ sec $\cdot$ cmHg |
| Oxygen | $228 \times 10^{-6}$ cm$^3$(STP)/cm$^2 \cdot$ sec $\cdot$ cmHg |
| Argon | $236 \times 10^{-6}$ cm$^3$(STP)/cm$^2 \cdot$ sec $\cdot$ cmHg |
| Nitrogen | $105 \times 10^{-6}$ cm$^3$(STP)/cm$^2 \cdot$ sec $\cdot$ cmHg |
| Carbon Dioxide | $1,360 \times 10^{-6}$ cm$^3$(STP)/cm$^2 \cdot$ sec $\cdot$ cmHg |
| Methane | $348 \times 10^{-6}$ cm$^3$(STP)/cm$^2 \cdot$ sec $\cdot$ cmHg |
| Ethane | $800 \times 10^{-6}$ cm$^3$(STP)/cm$^2 \cdot$ sec $\cdot$ cmHg |

We assumed the one-stage membrane separation operation as in FIG. 1. The stage-cut was assumed to be about 60%. The results of the calculations are shown in Table 10.

TABLE 10

| Component/Parameter | Stream 110 | Stream 116 | Stream 117 |
|---|---|---|---|
| Mass Flow Rate (lb/h) | 529.9 | 211.5 | 318.4 |
| Flow Rate (scfm) | 100 | 40.9 | 59.1 |
| Temperature (° C.) | 25 | 21 | 21 |
| Pressure (psia) | 115 | 115 | 20 |
| Component (mol %) | | | |
| Ethylene | 60.0 | 51.6 | 65.8 |
| Oxygen | 3.0 | 5.5 | 1.3 |
| Argon | 5.0 | 9.1 | 2.2 |
| Nitrogen | 7.0 | 14.9 | 1.5 |
| Carbon Dioxide | 20.0 | 12.8 | 25.0 |
| Methane | 2.5 | 4.0 | 1.5 |
| Ethane | 2.5 | 2.1 | 2.7 |
| Component (lb/h) | | | |
| Ethylene | 281.3 | 98.8 | 182.5 |
| Argon | 33.4 | 24.8 | 8.6 |

Membrane Area: 7 m$^2$

Example 11

Calculations were performed as in Example 10, except with a stage-cut of about 75%. The results of the calculations are shown in Table 11.

TABLE 11

| Component/Parameter | Stream 110 | Stream 116 | Stream 117 |
|---|---|---|---|
| Mass Flow Rate (lb/h) | 529.9 | 138.4 | 391.5 |
| Flow Rate (scfm) | 100 | 27.0 | 73.0 |
| Temperature (° C.) | 25 | 21 | 21 |
| Pressure (psia) | 115 | 115 | 20 |
| Component (mol %) | | | |
| Ethylene | 60.0 | 44.2 | 65.8 |
| Oxygen | 3.0 | 7.1 | 1.5 |
| Argon | 5.0 | 11.7 | 2.5 |
| Nitrogen | 7.0 | 21.0 | 1.8 |

TABLE 11-continued

| Component/Parameter | Stream 110 | Stream 116 | Stream 117 |
|---|---|---|---|
| Carbon Dioxide | 20.0 | 9.4 | 23.9 |
| Methane | 2.5 | 4.8 | 1.7 |
| Ethane | 2.5 | 1.8 | 2.7 |
| Component (lb/h) | | | |
| Ethylene | 281.3 | 56.0 | 225.3 |
| Argon | 33.4 | 21.0 | 12.4 |

Membrane Area: 9 m$^2$

Example 12

Calculations were performed as in Example 10, except with a stage-cut of about 90%. The results of the calculations are shown in Table 12.

TABLE 12

| Component/Parameter | Stream 110 | Stream 116 | Stream 117 |
|---|---|---|---|
| Mass Flow Rate (lb/h) | 529.9 | 61.7 | 468.2 |
| Flow Rate (scfm) | 100 | 12.2 | 87.8 |
| Temperature (° C.) | 25 | 21 | 21 |
| Pressure (psia) | 115 | 115 | 20 |
| Component (mol %) | | | |
| Ethylene | 60.0 | 24.3 | 64.9 |
| Oxygen | 3.0 | 10.4 | 2.0 |
| Argon | 5.0 | 16.8 | 3.4 |
| Nitrogen | 7.0 | 38.0 | 2.7 |
| Carbon Dioxide | 20.0 | 3.7 | 22.3 |
| Methane | 2.5 | 5.8 | 2.0 |
| Ethane | 2.5 | 1.0 | 2.7 |
| Component (lb/h) | | | |
| Ethylene | 281.3 | 13.9 | 267.4 |
| Argon | 33.4 | 13.7 | 19.7 |

Membrane Area: 12 m$^2$

Example 13

Table 13, compiled from information in Tables 10, 11, and 12, compares the ethylene losses and the ethylene recovery rates of the process of the invention at varying stage-cuts. As can be seen, the higher the stage-cut, the lower is the ethylene loss in the argon vent stream, and the greater is the ethylene recovery.

TABLE 13

| Parameter | No membrane | Table 10 | Table 11 | Table 12 |
|---|---|---|---|---|
| Stage-Cut (%) | — | 60 | 75 | 90 |
| Membrane Area (m$^2$) | — | 7 | 9 | 12 |
| Ethylene concentration in vent stream (mol %) | 60.0 | 51.6 | 44.2 | 24.3 |
| Amount of Ethylene in vent stream (lb/h) | 281.3 | 98.8 | 56.0 | 13.9 |
| Moles of ethylene lost/mole of argon vented | 12 | 4.0 | 2.7 | 1.0 |
| Removal/Recovery compared to No membrane (%) | — | 64.9 | 80.1 | 95.1 |

Examples 14–17

Ethylene Recovery at Constant Level of Argon Purge

Example 14

A series of computer calculations were performed with a modeling program, ChemCad III (ChemStations, Inc., Houston, Tex.), to illustrate the ethylene recovery that can be achieved when a constant level of argon removal is required.

The feed composition and membrane pressure-normalized fluxes were assumed to be as in Example 10. The stage-cut was assumed to be about 60%. Also as in Example 10, it was assumed that, absent the membrane recovery unit, the process vents about 33 lb of argon and 281 lb of ethylene per hour. The membrane process was configured to maintain this same argon purge rate. The results of the calculations are shown in Table 14.

TABLE 14

| Component/Parameter | Stream 110 | Stream 116 | Stream 117 |
| --- | --- | --- | --- |
| Mass Flow Rate (lb/h) | 713.2 | 284.7 | 428.5 |
| Flow Rate (scfm) | 134.6 | 55.0 | 79.6 |
| Temperature (° C.) | 25 | 21 | 21 |
| Pressure (psia) | 115 | 115 | 20 |
| Component (mol %) | | | |
| Ethylene | 60.0 | 51.6 | 65.8 |
| Oxygen | 3.0 | 5.5 | 1.3 |
| Argon | 5.0 | 9.1 | 2.2 |
| Nitrogen | 7.0 | 14.9 | 1.5 |
| Carbon Dioxide | 20.0 | 12.8 | 25.0 |
| Methane | 2.5 | 4.0 | 1.5 |
| Ethane | 2.5 | 2.1 | 2.7 |
| Component (lb/h) | | | |
| Ethylene | 378.6 | 133.0 | 245.6 |
| Argon | 44.9 | 33.4 | 11.5 |

Membrane Area: 9 m$^2$

The process vents 133 lb/h of ethylene compared to the no-membrane case in which 281 lb/h of ethylene was vented. Thus, a stage-cut of 60% yields an ethylene recovery of about 50%.

Example 15

Calculations were performed as in Example 14, except with a stage-cut of 75%. The results of the calculations are shown in Table 15.

TABLE 15

| Component/Parameter | Stream 110 | Stream 116 | Stream 117 |
| --- | --- | --- | --- |
| Mass Flow Rate (lb/h) | 841.4 | 219.7 | 621.7 |
| Flow Rate (scfm) | 158.8 | 42.9 | 115.9 |
| Temperature (° C.) | 25 | 21 | 21 |
| Pressure (psia) | 115 | 115 | 20 |
| Component (mol %) | | | |
| Ethylene | 60.0 | 44.2 | 65.8 |
| Oxygen | 3.0 | 7.1 | 1.5 |
| Argon | 5.0 | 11.7 | 2.5 |
| Nitrogen | 7.0 | 21.0 | 1.8 |
| Carbon Dioxide | 20.0 | 9.4 | 23.9 |
| Methane | 2.5 | 4.8 | 1.7 |
| Ethane | 2.5 | 1.8 | 2.7 |
| Component (lb/h) | | | |
| Ethylene | 446.7 | 88.9 | 357.8 |
| Argon | 53.0 | 33.4 | 19.6 |

Membrane Area: 14 m$^2$

In this case, the process vents about 90 lb/h of ethylene compared to the no-membrane case in which 281 lb/h of ethylene was vented. In other words, the ethylene recovery is nearly 70%.

Example 16

Calculations were performed as in Example 14, except with a stage-cut of 90%. The results of the calculations are shown in Table 16.

TABLE 16

| Component/Parameter | Stream 110 | Stream 116 | Stream 117 |
| --- | --- | --- | --- |
| Mass Flow Rate (lb/h) | 1,295.5 | 150.8 | 1,144.7 |
| Flow Rate (scfm) | 244.5 | 29.7 | 214.8 |
| Temperature (° C.) | 25 | 21 | 21 |
| Pressure (psia) | 115 | 115 | 20 |
| Component (mol %) | | | |
| Ethylene | 60.0 | 24.3 | 64.9 |
| Oxygen | 3.0 | 10.4 | 2.0 |
| Argon | 5.0 | 16.8 | 3.4 |
| Nitrogen | 7.0 | 38.0 | 2.7 |
| Carbon Dioxide | 20.0 | 3.7 | 22.3 |
| Methane | 2.5 | 5.8 | 2.0 |
| Ethane | 2.5 | 1.0 | 2.7 |
| Component (lb/h) | | | |
| Ethylene | 687.8 | 33.9 | 653.9 |
| Argon | 81.6 | 33.4 | 48.2 |

Membrane Area: 29 m$^2$

In this case, the process vents only about 33 lb/h of ethylene compared to the no-membrane case in which 281 lb/h of ethylene was vented. This represents an ethylene recovery of about 90%.

Example 17

Table 17, compiled from Tables 14, 15, and 16, compares the ethylene losses and the ethylene recovery rates of the process of the invention at varying stage-cuts. As can be seen, the higher the stage-cut, the lower is the ethylene loss in the argon vent stream, and the greater is the ethylene recovery, while still maintaining the 33-lb/h argon purge rate.

TABLE 17

| Parameter | No membrane | Table 14 | Table 15 | Table 16 |
| --- | --- | --- | --- | --- |
| Stage-Cut (%) | — | 60 | 75 | 90 |
| Membrane Area (m$^2$) | — | 9 | 14 | 29 |
| Ethylene concentration in vent stream (mol %) | 60.0 | 51.2 | 44.2 | 24.3 |
| Amount of Ethylene in vent stream (lb/h) | 281.3 | 133.0 | 88.9 | 33.9 |
| Removal/Recovery compared to No membrane (%) | — | 52.7 | 68.4 | 87.9 |

The ethylene recovery rates shown in Tale 17 are slightly lower than those shown in Table 13.

We claim:

1. A process for producing vinyl acetate, comprising the following steps:
   (a) reacting ethylene, acetic acid and oxygen in a reactor to form vinyl acetate;
   (b) withdrawing from said reactor a crude product stream comprising vinyl acetate, ethylene and argon;
   (c) removing at least a portion of said vinyl acetate from said crude product stream to form a non-product stream;
   (d) providing a membrane having a feed side and a permeate side, and being selectively permeable to ethylene over argon;

(e) passing at least a portion of said non-product stream across said feed side under conditions in which there is a pressure drop from said feed side to said permeate side;

(f) withdrawing from said feed side an argon-rich purge stream enriched in argon and depleted in ethylene compared with said non-product stream;

(g) withdrawing from said permeate side an ethylene-rich permeate stream enriched in ethylene and depleted in argon compared with said non-product stream;

(h) recirculating at least a portion of said ethylene-rich permeate stream to said reactor.

2. The process of claim 1, wherein said process is characterized by a stage-cut between said ethylene-rich permeate stream and said non-product stream of at least about 30%.

3. The process of claim 1, wherein said membrane comprises a rubbery polymer.

4. The process of claim 1, wherein said membrane comprises silicone rubber.

5. The process of claim 1, wherein said membrane has an ethylene/argon selectivity of at least about 4.

6. The process of claim 1, wherein said ethylene-rich permeate stream contains at least 50% of the ethylene that was present in said portion of said non-product stream.

7. The process of claim 1, wherein said ethylene-rich permeate stream contains at least 70% of the ethylene that was present in said portion of said non-product stream.

8. The process of claim 1, wherein said ethylene-rich permeate stream contains at least 90% of the ethylene that was present in said portion of said non-product stream.

9. The process of claim 1, wherein said non-product stream further comprises carbon dioxide and wherein at least a portion of said non-product stream is treated to remove carbon dioxide and then recirculated to said reactor.

10. The process of claim 1, wherein said non-product stream further comprises carbon dioxide and wherein said portion of said non-product stream is treated to at least partially remove carbon dioxide prior to carrying out said step (e).

11. A process for treating a purge stream from an vinyl acetate manufacturing process, said purge stream comprising ethylene and argon, said process comprising the following steps:

(a) providing a membrane having a feed side and a permeate side, and being selectively permeable to ethylene over argon;

(b) passing at least a portion of said purge stream across said feed side under conditions in which there is a pressure drop from said feed side to said permeate side;

(c) withdrawing from said feed side an argon-rich stream enriched in argon and depleted in ethylene compared with said purge stream;

(d) withdrawing from said permeate side an ethylene-rich permeate stream enriched in ethylene and depleted in argon compared with said purge stream;

(e) recirculating at least a portion of said ethylene-rich permeate stream to said vinyl acetate manufacturing process.

12. The process of claim 11, wherein said process is characterized by a stage-cut between said ethylene-rich permeate stream and said purge stream of at least about 30%.

13. The process of claim 11, wherein said membrane comprises a rubbery polymer.

14. The process of claim 11, wherein said membrane comprises silicone rubber.

15. The process of claim 11, wherein said membrane has an ethylene/argon selectivity of at least about 4.

16. The process of claim 11, wherein said ethylene-rich permeate stream contains at least 50% of the ethylene that was present in said portion of said purge stream.

17. The process of claim 11, wherein said ethylene-rich permeate stream contains at least 70% of the ethylene that was present in said portion of said purge stream.

18. The process of claim 11, wherein said ethylene-rich permeate stream contains at least 90% of the ethylene that was present in said portion of said purge stream.

19. A process for producing vinyl acetate, comprising the following steps:

(a) reacting ethylene, acetic acid and oxygen in a reactor to form vinyl acetate;

(b) withdrawing from said reactor a crude product stream comprising vinyl acetate, ethylene and argon;

(c) removing at least a portion of said vinyl acetate from said crude product stream to form a non-product stream;

(d) compressing said non-product stream;

(e) providing a membrane having a feed side and a permeate side, and being selectively permeable to ethylene over argon;

(f) passing at least a portion of said non-product stream across said feed side under conditions in which there is a pressure drop from said feed side to said permeate side;

(g) withdrawing from said feed side an argon-rich purge stream enriched in argon and depleted in ethylene compared with said non-product stream;

(h) withdrawing from said permeate side an ethylene-rich permeate stream enriched in ethylene and depleted in argon compared with said non-product stream;

(i) recirculating at least a portion of said ethylene-rich permeate stream to said compressing step (d).

20. The process of claim 19, wherein said process is characterized by a stage-cut between said ethylene-rich permeate stream and said non-product stream of at least about 30%.

21. The process of claim 19, wherein said membrane comprises silicone rubber.

22. The process of claim 19, wherein said ethylene-rich permeate stream contains at least 50% of the ethylene that was present in said portion of said non-product stream.

23. The process of claim 19, wherein said non-product stream further comprises carbon dioxide and wherein at least a portion of said non-product stream is treated to remove carbon dioxide and then recirculated to said reactor.

24. A process for producing vinyl acetate, comprising the following steps:

(a) reacting ethylene, acetic acid and oxygen in a reactor to form vinyl acetate;

(b) withdrawing from said reactor a crude product stream;

(c) passing said crude product stream to one or more purification steps to produce a vinyl acetate stream, and a non-product stream comprising ethylene and argon;

(d) providing a membrane having a feed side and a permeate side, and being selectively permeable to ethylene over argon;

(e) passing at least a portion of said non-product stream across said feed side under conditions in which there is a pressure drop from said feed side to said permeate side;

(f) withdrawing from said feed side an argon-rich purge stream enriched in argon and depleted in ethylene compared with said non-product stream;

(g) withdrawing from said permeate side an ethylene-rich permeate stream enriched in ethylene and depleted in argon compared with said non-product stream;

(h) recirculating at least a portion of said ethylene-rich permeate stream to said one or more purification steps.

25. The process of claim 24, wherein said process is characterized by a stage-cut between said ethylene-rich permeate stream and said non-product stream of at least about 30%.

26. The process of claim 24, wherein said membrane comprises silicone rubber.

27. The process of claim 24, wherein said ethylene-rich permeate stream contains at least 50% of the ethylene that was present in said portion of said non-product stream.

28. The process of claim 24, wherein said non-product stream further comprises carbon dioxide and wherein at least a portion of said non-product stream is treated to remove carbon dioxide and then recirculated to said reactor.

29. The process of claim 19, wherein said membrane has an ethylene/argon selectivity of at least about 4.

30. The process of claim 24, wherein said membrane has an ethylene/argon selectivity of at least about 4.

31. The process of claim 1, wherein said process is characterized by a stage-cut between said ethylene-rich permeate stream and said non-product stream of at least about 40%.

32. The process of claim 1, wherein said process is characterized by a stage-cut between said ethylene-rich permeate stream and said non-product stream of at least about 50%.

33. The process of claim 11, wherein said process is characterized by a stage-cut between said ethylene-rich permeate stream and said non-product stream of at least about 40%.

34. The process of claim 11, wherein said process is characterized by a stage-cut between said ethylene-rich permeate stream and said non-product stream of at least about 50%.

35. The process of claim 19, wherein said process is characterized by a stage-cut between said ethylene-rich permeate stream and said non-product stream of at least about 40%.

36. The process of claim 19, wherein said process is characterized by a stage-cut between said ethylene-rich permeate stream and said non-product stream of at least about 50%.

37. The process of claim 24, wherein said process is characterized by a stage-cut between said ethylene-rich permeate stream and said non-product stream of at least about 40%.

38. The process of claim 24, wherein said process is characterized by a stage-cut between said ethylene-rich permeate stream and said non-product stream of at least about 50%.

* * * * *